United States Patent [19]

De Paulis et al.

[11] Patent Number: 4,937,260
[45] Date of Patent: * Jun. 26, 1990

[54] BENZAMIDO-DERIVATIVES

[75] Inventors: Tomas De Paulis, Nashville, Tenn.; Sten I. Rämsby, Södertälje; Sven O. Ögren, Nykvarn, both of Sweden

[73] Assignee: Astra Lakemedal Aktiebolag, Sodertalje, Sweden

[*] Notice: The portion of the term of this patent subsequent to Dec. 6, 2005 has been disclaimed.

[21] Appl. No.: 148,104

[22] Filed: Jan. 27, 1988

Related U.S. Application Data

[63] Continuation-in-part of Ser. No. 529,326, Sep. 2, 1983, abandoned.

[30] Foreign Application Priority Data

Sep. 9, 1982 [SE] Sweden .................................. 8205135

[51] Int. Cl.$^5$ ..................... C07D 207/09; A61K 31/40
[52] U.S. Cl. ...................................... 514/428; 548/567
[58] Field of Search ......................... 548/567; 514/428

[56] References Cited

U.S. PATENT DOCUMENTS

| | | | |
|---|---|---|---|
| 3,342,826 | 9/1967 | Miller et al. | 260/294 |
| 3,793,030 | 2/1974 | Asami | 96/91 R |
| 3,862,139 | 1/1975 | Podesva et al. | 424/274 X |
| 3,914,418 | 10/1975 | Patchett et al. | 424/230 |
| 4,021,567 | 5/1977 | Kaplan et al. | 424/274 |
| 4,029,678 | 6/1977 | Bulteau et al. | 424/274 X |
| 4,232,037 | 11/1980 | Florvall et al. | 548/567 X |
| 4,789,683 | 12/1988 | Florvall | 548/567 |

FOREIGN PATENT DOCUMENTS

| | | |
|---|---|---|
| 0695272 | 3/1967 | Belgium . |
| 0060235 | 9/1982 | European Pat. Off. . |
| 0053584 | 6/1988 | European Pat. Off. . |
| 2459221 | 6/1975 | Fed. Rep. of Germany . |
| 2803651 | 8/1978 | Fed. Rep. of Germany . |
| 2901170 | 7/1979 | Fed. Rep. of Germany . |
| 2939914 | 4/1980 | Fed. Rep. of Germany . |
| 0060756 | 11/1965 | German Democratic Rep. . |
| 0019447 | 9/1978 | Japan . |
| 1234118 | 6/1971 | United Kingdom . |
| 1508880 | 4/1978 | United Kingdom . |

OTHER PUBLICATIONS

Banker et al., Modern Pharmaceutics (date not available), pp. 565-566, Morcel Dekker, Inc., N.Y. and Basel.

Pharmaceutics and Pharmacy Practice, Banker et al., (date not available, p. 118, J. B. Lippincott Co., Phila. and Toronto.

Doc. No. 0032712, date not given, Israel, abstract only considered.

Doc. No. 005916M, 1/21/66, French Medicament, abstract only considered.

Chemical Abstracts, vol. 86:148800g, 1977, "Thermal Development Type Diazo Copying Materials".

*Primary Examiner*—Joseph Paul Brust
*Attorney, Agent, or Firm*—White & Case

[57] ABSTRACT

Novel therapeutically active compounds of the formula

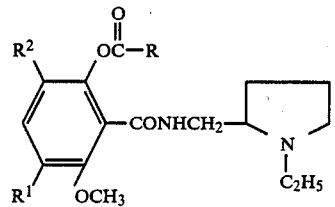

wherein R is a straight or branched alkyl group with 6-18 carbon atoms, $R^1$ is hydrogen, chlorine, bromine or an alkyl group with 1-3 carbon atoms and $R^2$ is chlorine, bromine or an alkyl group with 1-3 carbon atoms; or a physiologically acceptable salt or an optical isomer thereof, methods and intermediates for their preparation, pharmaceutical preparations containing them and methods for their therapeutical use.

11 Claims, No Drawings

BENZAMIDO-DERIVATIVES

This application is a continuation-in-part of application Ser. No. 529,326, filed on 9/2/83.

DESCRIPTION

1. Field of the Invention

The present invention relates to novel, pharmacologically active derivatives of benzamide, intermediates and processes for their preparation, pharmaceutical compositions containing the benzamido-derivatives and to methods of their pharmacological use.

The object of the invention is to provide a benzamido-derivative useful in the treatment of emesis, psychosomatic diseases and psychiatric disorders.

2. Prior Art

Sulpiride, (U.S. Pat. No. 3 342 826) with the formula

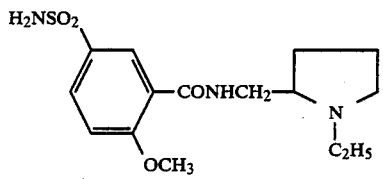

is a recently marketed antipsychotic agent. Sulpiride produces weak extrapyramidal side effects in humans and weak catalepsy in experimental animals.

In U.S. Pat. No. 4 232 037 antipsychotic compounds of the formula

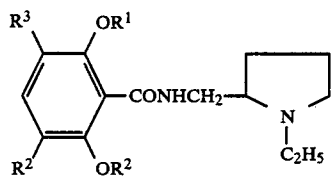

wherein $R^1$ is an alkyl group with 1–3 carbon atoms, $R^2$ and $R^3$ are the same or different and each is hydrogen, chlorine or bromine, are described. Among these compounds the compound of the formula

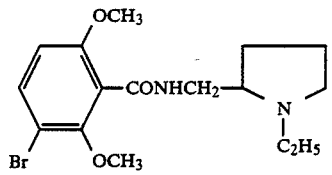

and with the designated FLA 731, is disclosed. The compounds of the U.S. Pat. No. 4 232 037 have a less potent antipsychotic effect than the compounds of the present invention.

DISCLOSURE OF THE INVENTION

The present invention relates to compounds of the formula

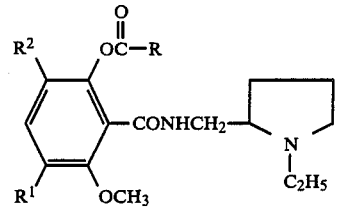

I wherein R is a straight or branched alkyl group with 6–18 carbon atoms, $R^1$ is hydrogen, chlorine, bromine or an alkyl group with 1–3 carbon atoms and $R^2$ is chlorine, bromine or an alkyl group with 1–3 carbon atoms; or a physiologically acceptable salt or an optical isomer thereof.

It has been found that such compounds have valuable therapeutical properties.

The invention thus provides compounds, and physiologically acceptable salts thereof, which compounds are useful in therepeutic treatment of emesis, of psychosomatic diseases such as gastric and duodenal ulcer, and of psychiatric disorders such as depression, anxiety and especially psychoses, e.g. schizofrenia. The compounds have a prolonged time of action, particularly those in which R is a straight or branched chain alkyl group with 13–18 carbon atoms.

Alkyl groups with 1–3 carbon atoms in formula I are straight or branched alkyl groups, such as methyl, ethyl, n-propyl and isopropyl.

Straight or branched alkyl groups with 6–18 carbon atoms are of the formula

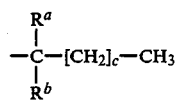

wherein c is an integer 0–16 and $R^a$ and $R^b$ are the same or different and each is H, $CH_3$ or $C_2H_5$ and the total number of carbon atoms in the moiety is at least 6 and at most 18.

Examples of straight or branched alkyl groups with 6–18 carbon atoms are

—(CH$_2$)$_8$CH$_3$     —CH(C$_2$H$_5$)CH$_2$CH$_2$CH$_2$CH$_3$

—CH(CH$_3$)CH$_2$CH$_2$CH$_2$CH$_3$

—C(C$_2$H$_5$)$_3$

—(CH$_2$)$_{14}$CH$_3$

The new compounds of this invention may be used therapeutically as the racemic mixtures of (+)- and (−)-forms, which are obtained by synthesis. They may also be resolved into the corresponding enantiomers which, likewise, may be used in therapy. The (+)- and (−)-forms may also be obtained by the reaction of the corresponding enantiomeric 2-(aminomethyl)-1-alkyl-/alkenylpyrrolidine with the benzoic acid moiety.

The starting materials are known or may, if they are novel, be obtained according to processes known per se.

The compounds of this invention may be administered in the form of free bases or their salts with non-toxic acids. Some typical examples of these salts are the hydrobromide, hydrochloride, phosphate, sulphate, sulphonate, citrate, lactate, maleate and tartrate.

PHARMACEUTICAL PREPARATIONS

In clinical practice the compounds of the present invention will normally be administered orally, rectally or by injection in the form of pharmaceutical preparations comprising the active ingredient either as a free base or as a pharmaceutically acceptable non-toxic, acid addition salt, e.g. the hydrochloride, hydrobromide, lactate, acetate, sulphate, sulphonate and the like in association with a pharmaceutically acceptable carrier. Accordingly, terms relating to the novel compounds of this invention whether generically or specifically are intended to include both the free amine base and the acid addition salts of the free base, unless the context in which such terms are used, e.g. in the specific examples would be inconsistent with the broad concept.

The carrier may be a solid, semisolid or liquid diluent or capsule. These pharmaceutical preparations constitute a further aspect of this invention. Usually the active substance will constitute between 0.1 and 99% by weight of the preparation, more specifically between 0.5 and 20% by weight for preparation intended for injection and between 2 and 50% by weight for preparations suitable for oral administration.

To produce pharmaceutical preparations containing a compound of the invention in the form of dosage units for oral application, the selected compound may be mixed with a solid pulverulent carrier, e.g. lactose, saccharose, sorbitol, mannitol, starches such as potato starch, corn starch or amylopectin, cellulose derivatives, or gelatine, and a lubricant such as magnesium stearate, calcium stearate, polyethylene glycol waxes, and the like, and then compressed to form tablets. If coated tablets are required, the cores, prepared as described above, may be coated with a concentrated sugar solution which may contain, e.g. gum arabic, gelatine, talcum, titanium dioxide, and the like. Alternatively, the tablet can be coated with a lacquer dissolved in a readily volatile organic solvent or mixture of organic solvents. Dyestuffs may be added to these coatings in order to readily distinguish between tablets containing different active substances or different amounts of the active compound.

For the preparation of soft gelatine capsules (pearl-shaped capsules) consisting of gelatine and for example, glycerol or similar closed capsules, the active substance may be admixed with a vegetable oil. Hard gelatine capsules may contain granulates of the active substance in combination with solid, pulverulent carriers such as lactose, saccharose, sorbitol, mannitol, starches (e.g. potato starch, corn starch or amylopectin), cellulose derivatives or gelatine.

Dosage units for rectal application can be prepared in the form of suppositories comprising the active substance in admixture with a neutral fatty base, or gelatine rectal capsules comprising the active substance in admixture with vegetable oil or paraffin oil.

Liquid preparations for oral application may be in the form of syrups or suspensions for example, solutions containing from about 0.2% to about 20% by weight of the active substance herein described, the balance being sugar and a mixture of ethanol, water, glycerol and propyleneglycol. Optionally such liquid preparations may contain colouring agents, flavouring agents, saccharine and carboxymethylcellulose as a thickening agent.

Solutions for parenteral applications by injection can be prepared in an aqueous solution of a water-soluble pharmaceutically acceptable salt of the active substance preferably in a concentration of from about 0.5% to about 10% by weight. These solutions may also contain stabilizing agents and/or buffering agents and may conveniently be provided in various dosage unit ampoules.

A preferred embodiment of the present invention is a pharmceutical depot preparation for subcutaneous or intramuscular administration containing as active ingredient a compound of the formula I above. Suitable peroral daily doses of the compounds of the invention are 100–500 mg, preferably 200–300 mg. Depot administration can be performed in dosages of 25–2000 mg every 1 to 3 weeks.

METHODS OF PREPARATION

The compounds of the invention may be obtained by one of the following methods.

A. The compounds of the formula

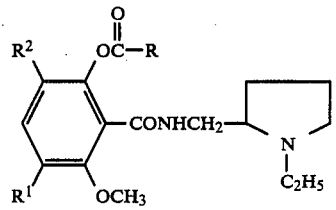

I wherein R is a straight or branched alkyl group with 6–18 carbon atoms, $R^1$ is hydrogen, chlorine, bromine or an alkyl group with 1–3 carbon atoms and $R^2$ is chlorine, bromine or an alkyl group with 1–3 carbon atoms can be obtained by reaction of a compound of the formula

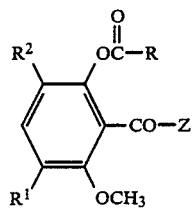

II wherein $R^1$, $R^2$ and R have the definition given above and -CO-Z is a reactive group capable of reacting with an amino group under formation of an amide moiety with a compound of the formula

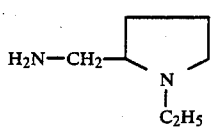

III or a reactive derivative thereof.

The reaction is carried out in a suitable solvent, such as diethyl ether, acetone, methylethyl ketone, chloroform or toluene between 0° C. and the boiling point of the reaction mixture. The resulting amine hydrochloride salt is readily recovered e.g. by filtration. Alternatively, the obtained salt is dissolved in water and converted to the free base using conventional techniques, such as the addition of sodium hydroxide solution.

Z is the acylating group -CO-Z may be a halogen group, such as chlorine or bromine, a hydroxy group or an organic residue.

The organic residue comprises groups which can form reactive said derivatives. These can be carboxylic acid esters, e.g. methyl, ethyl, propyl, butyric, isobutyric and pentyl esters or comparable reactive esters, e.g. cyanomethyl or methoxymethyl ester, N-hydroxyimido ester or substituted or unsubstituted aromatic esters; acid hydrozides; acid azides; symmetrical anhydrides; mixed anhydrides for instance formed with lower alkylhalogenformates; azolides, e.g. triazolide, tetrazolide or imidazolide; or acid isocyanates.

According to the invention the following compounds can be used as reactive derivatives of the amine III: Reaction products of the amine with phosphorus chloride, phosphorus oxychloride, dialkyl, diaryl or o-phenylenechlorophosphites or alkyl or aryldichlorophosphites, or an isothiocyanates of the amine. The mentioned reactive derivatives can be reacted with the acid in situ or after previous isolation.

It is also possible to react the free acid and the free amine in the presence of a condensating agent, e.g. silicon tetrachloride, diphosphoruspentoxide or carbodiimides such as dicyclohexylcarbodiimide, N,N'-carbonyldiimidazole, N,N'-thionyldiimidazole and diethyldiazodicarboxylate.

B. The compounds of the formula

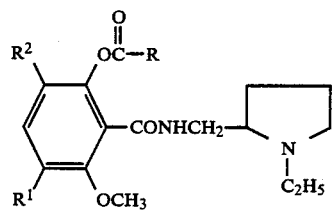

wherein $R^1$, $R^2$ and R have the definition given above can be obtained by N-alkylation of a compound of the formula

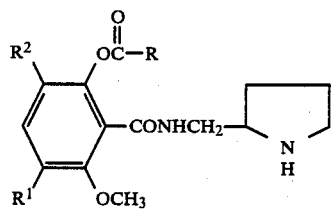

wherein $R^1$, $R^2$ and R have the definition given above, with a compound of the formula $C_2H_5-X$ wherein X is chlorine, bromine, sulphate, phosphate, benzenesulphonate or toluenesulphonate.

The reaction can be effected by treating the reactants at 50°-100° C. in a suitable solvent, e.g. acetone, alcohols, dimethylformamide (DMF), dimethylsulphoxide (DMSO) in the presence of a base, for example NaOH or $K_2CO_3$.

C. The compounds of the formula

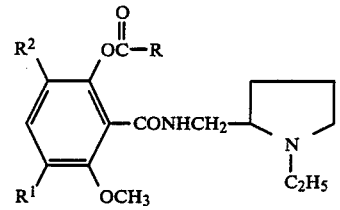

wherein $R^1$, $R^2$ and R have the definition given above can be obtained by reaction of a compound of the formula

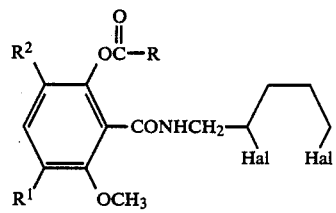

wherein $R^1$, $R^2$ and R have the definition given above and Hal is Cl or Br with a compound of the formula $C_2H_5NH_2$ The reaction is performed with the amine in excess, either without solvent or with a suitable solvent, such as lower alcohols, halogenated aliphatic hydrocarbons, DMF, DMSO at temperatures from 0° C. to 100° C.

D. The compounds of the formula

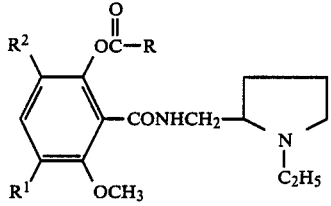

wherein $R^1$, $R^2$ and R have the definition given above can be obtained by reduction of a compound of the formula

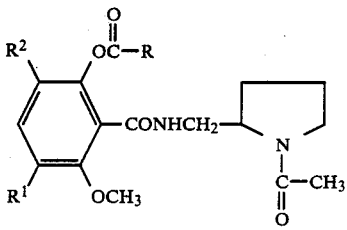

wherein $R^1$, $R^2$ and R have the definition given above.

Suitable reducing agents working on the less sterically hindered amide group are (a) $LiAlH_4$ and alkoxy complexes thereof; (b) $NaBH_4$ with addition of transition metal salts, or $AlCl_3$ or $BF_3$ or $POCl_3$ or carboxylic acids such as $CH_3COOH$ and $CF_3COOH$; (c) $B_2H_6$.

The reaction is effected in alkyl ethers, such as diethylether, dimethoxyethane, diglyme, THF, dioxane, at temperatures from 0° C. to reflux temperatures of the reaction mixtures.

E. The compounds of the formula

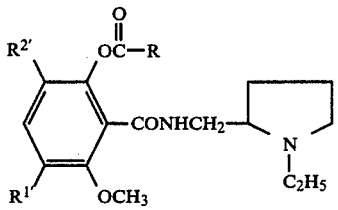

wherein R has the definition given above and $R^{1'}$ and/or $R^{2'}$ is Cl, Br or an alkyl (1–3C) group, and the other, when necessary, a hydrogen atom, can be obtained by reaction of a Cl/Br agent or an alkylating agent with a compound of the formula

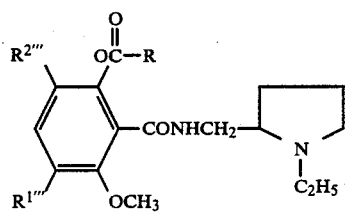

wherein R has the definition given above and $R^{1''''}$ and $R^{2''''}$ are hydrogen or $R^{1''''}$ or $R^{2''''}$ is $R^1=R^2$ as defined above.

Halogenation can be performed with halogen or a halogendioxane complex or with a sulphurylhalogenide (preferably sulphurylchloride).

Alkylation can be performed with an alkylhalide with Lewis acid catalysts.

Chlorination is effected by heating the starting compound with chlorine with or without Lewis acid catalysis or with HOCl, N-chloroamides in the presence of acid catalyst in suitable solvent e.g. chloroform, nitrobenzene.

Bromination is carried out with $Br_2$ with or without Lewis acid catalysis or bromination in acetic acid in the presence of a base e.g. sodium acetate or by using brominedioxane complex. Other reagents can be used among them HOBr and N-bromoamides expecially N-bromosuccinimide with acid catalysis.

Alkylations are performed by using well-known Friedel-Crafts procedures.

F. The compound of the formula

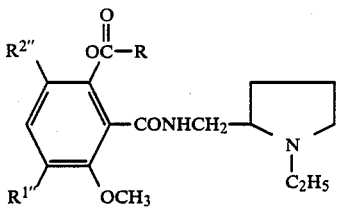

wherein R has the definition given above and $R^{1'''}$ and/or $R^{2'''}$ is Cl or Br and the other, when necessary, a hydrogen atom, can be obtained by the reaction in a first step with $NaNO_2$ and in a second step with cuprous halogenide of a compound of the formula

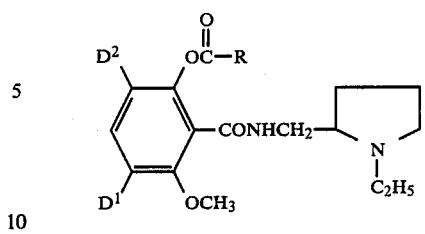

wherein R has the definition given above and $D^1$ and $D^2$ are the same or different and each represents a hydrogen atom or an amino group and at least one of $D^1$ and $D^2$ is an amino group.

Diazotation is performed in water at 0° C. with $NaNO_2$ in the presence of mineral acid. Compounds where $R^{1''}$ and $R^{2''}$ are Cl or Br are prepared by using a Sandmeyer reaction with CuBr or CuCl.

G. The compounds of the formula

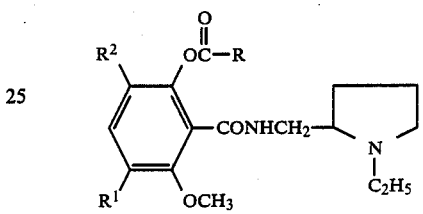

wherein $R^1$, $R^2$ and R have the definition given above, can be obtained by reaction of a compound of the formula

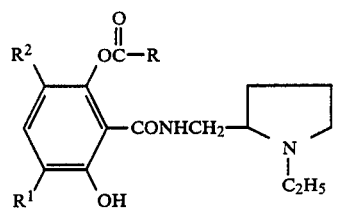

wherein $R^1$, $R^2$ and R have the definition given above, with a compound of the formula $CH_3B$ wherein B is $-(SO_4)_{\frac{1}{2}}$, $-(PO_4)_{\frac{1}{3}}$ or halogen.

The reaction is effected selectively in a suitable solvent, e.g. acetone, DMF at elevated temperatures with one equivalent of alkylating agent in the presence of base, e.g. alkali metal carbonates or hydroxides.

H. The Compounds of the formula

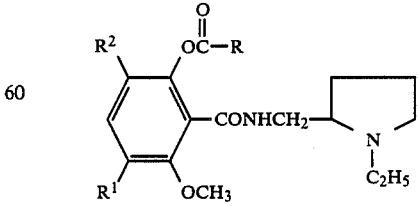

wherein $R^1$, $R^2$ and R have the definition given above can be obtained by reaction of a compound of the formula

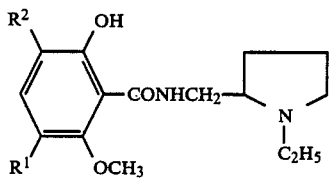

wherein $R^1$ and $R^2$ have the definition given above, with a compound of the formula

R-CO-Z' wherein R has the above given definition and Z' is Cl or Br.

The compounds are prepared by the reaction with the appropriate acid halide without solvent or in a suitable solvent such as $CF_3COOH$ with acid catalysis or by using a tertiary amine as solvent and/or catalyst.

INTERMEDIATES

The compounds of the formula

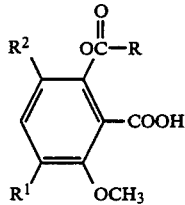

wherein R is a straight or branched alkyl group with 6-18 carbon atoms, $R^1$ is hydrogen, chlorine, bromine or an alkyl group with 1-3 carbon atoms and $R^2$ is chlorine, bromine or an alkyl group with 1-3 carbon atoms, are valuable intermediates for the preparation of the compounds of this invention by the process A.

The intermediate benzoic acids can be prepared by reacting a compound of the formula

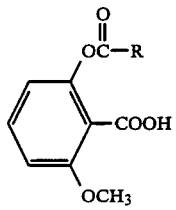

as follows:
(a) when $R^1$ and/or $R^2$ is Cl or Br: by chlorination or bromination for example as described under Method E above;
(b) when $R^1$ and/or $R^2$ is alkyl (1-3c): by reacting with an alkylhalide for example as described under Method E above;

Any of free acids can be converted to a compound of the formula II by esterification with for instance an acylhalogenide, an acylanhydride, a halogen formic acid ester or a dialkylcarbamyl halide.

BEST MODE OF CARRYING OUT THE INVENTION

The following illustrates the principle and the adoption of the invention, however, without being limited thereto.

EXAMPLE 1

S-(-)-2-decanoyloxy-3,5-diethyl-N-[(1-ethyl-2-pyrrolidinyl)methyl]-6-methoxybenzamide (FLB 427)

(-)-3,5-diethyl-N-[(1-ethyl-2-pyrrolidinyl)methyl]-2-hydroxy-6-methoxybenzamid hydrochloride (1.85 g, 0.005 mol) was dissolved in 10 ml trifluoroacetic acid. Decanoic acid chloride was added at 21° C. The reaction mixture was stirred over night followed by evaporation of the solvent. A saturated solution of potassium bicarbonate was added to the residue and the product was extracted with ether. Drying ($MgSO_4$) and evaporation gave 2.1 g (86%) of the decanoate ester as an oil. Thin layer chromatography on silica gel with a solvent mixture of $CH_2Cl_2$ and 3.5M $NH_3$ in ethanol (19:1) shows a new spot at Rf 0.56 compared to Rf 0.63 for the starting material. The mass spectrum of the ester has a molecular peak at m/e 488.

In a similar manner the following alkanoate esters were prepared from the corresponding 2-hydroxy benzamides and characterized on TLC on silica gel with solvent mixtures as defined in each example.

EXAMPLE 2

S-(-)-b 3-bromo-2-decanoyloxy-N-[(1-ethyl-2-pyrrolidinyl)methyl]-6-methoxybenzamide (FLB 422)

Rf 0.28 compared to Rf 0.38 for the starting material in $CH_2Cl_2$-EtOH-$NH_3$ (80:20:1). Mass spectrum m/e 510/512.

EXAMPLE 3

S-(-)-5-bromo-2-decanoyloxy-3-ethyl-N-[(1-ethyl-2-pyrrolidinyl)methyl]-6-methoxybenzamide

EXAMPLE 4

S-(-)-3,5-dichloro-(2-ethyl-hexanoyloxy)-N-[(1-ethyl-2-pyrrolidinyl)methyl]-6-methoxybenzamide (FLB 567)

Rf 0.64 in $CH_2Cl_2$-EtOH (4:1). Rf 0.23 in i-$Pr_2$O-MeOH (1:4).

EXAMPLE 5

S-(-)-5-chloro-2-decanoyloxy-3-ethyl-N-[(1-ethyl-2-pyrrolidinyl)methyl]-6-methoxybenzamide (FLB 492)

Rf 0.56 in $CH_2Cl_2$-EtOH (4:1). Rf 0.30 in i-$Pr_2$O-MeOH (1:4).

EXAMPLE 6

S-(-)-3,5-dichloro-2-nonanoyloxy-N-[(1-ethyl-2-pyrrolidinyl)methyl]-6-methoxybenzamide (FLB 501)

Rf 0.49 in $CH_2Cl_2$-EtOH (4:1). Rf 0.13 in i-$Pr_2$O-MeOH (1:4).

EXAMPLE 7

S-(-)-2-decanoyloxy-3,5-dibromo-N-[(1-ethyl-2-pyrrolidinyl)methyl]-6-methoxybenzamide

EXAMPLE 8

S-(-)-3,5-dichloro-2-α-ethylvaleroyloxy-N-[(-ethyl-2-pyrrolidinyl)methyl]-6-methoxybenzamide

EXAMPLE 9

S-(-)-2-decanoyloxy-3,5-dichloro-N-[(1-ethyl-2-pyrrolidinyl)methyl]-6-methoxybenzamide (FLB 491)

Rf 0.50 in $CH_2Cl_2$-EtOH (1:4). Rf 0.14 in i-$Pr_2O$-MeOH (4:1).

EXAMPLE 10

S-(-)-3,5-dichloro-2-α,α-diethylbutyroyloxy-N-[(1-ethyl-2-pyrrolidinyl)methyl]-6-methoxybenzamide

EXAMPLE 11

The following examples illustrate the preparation of pharmaceutical compositions of the invention. The wording "active substance" denotes a compound according to the present invention or a salt thereof.

EXAMPLE 12

S-(-)-3,5-dichloro-2-palmitoyloxy-N[(1-ethyl-2-pyrrolidinyl)methyl]-6-methoxybenzamide (S)(-)-3,5-dichloro-N[(1-ethyl-2-pyrrolidinyl)methyl]-2-hydroxy-6-methoxybenzamide (17.3 g, 0.05 mol) was dissolved in 100 ml of cyclohexane and 8.5 ml of trifluoroacetic acid. Palmitoyl chloride (16.5 g, 0.06 mol) dissolved in 10 ml of cyclohexane was added and the solution was refluxed at 100° C. under nitrogen atmosphere for 20 h. After cooling the solvent was evaporated in vacuo. The residual crystal mass was dissolved in ether and washed with a saturated potassium bicarbonate solution several times. Drying ($MgSO_4$) and evaporation of the solvent gave a yellow viscous oil (23.5 g) that crystallizes on cooling. The crude product was purified by rapid filtration through a $Al_2O_3$-column (500 g) using ether as the eluent. The eluent was evaporated affording the title compound as a viscous oil which crystallizes on standing. Yield 16.6 g (57%). Recrystallization from acetonitrile afforded an analytical sample having m.p. 34°–36° C. TLC-analysis showed one spot ($R_f$-value 0.36) on silica plates with 20% methanol in isopropyl ether as eluent.

NMR ($^1H$ and $^{13}C$) and MS (chemical ionization) spectra are consistent with the structure.

EXAMPLE 13

(S)(-)-3,5-dichloro-2-stearoyloxy-N[(ethyl-2-pyrrolidinyl)methyl]-6-methoxybenzamide This compound was prepared in an analogous manner as in the preceding example. $R_f$ value 0.44 in the same solvent system. The compound was recrystallized from acetonitrile and had m.p. 53°–54° C.

NMR ($^1H$ and $^{13}C$) and MS (chemical ionization) spectra were consistent with the structure.

FORMULATION A. SOFT GELATIN CAPSULES 500 g of active substance were mixed with 500 g of corn oil, whereupon the mixture was filled in soft gelatin capsules, each capsule containing 100 mg of the mixture (i.e. 50 mg of active substance).

FORMULATION B. SOFT GELATIN CAPSULES 500 g of active substance were mixed with 750 g of peanut oil, whereupon the mixture was filled in soft gelatin capsules, each capsule containing 125 mg of the mixture (i.e. 50 mg of active substance).

FORMULATION C. TABLETS 50 kg of active substance were mixed with 20 kg of silicic acid of the trade mark Aerosil. 45 kg of potato starch and 50 kg of lactose were mixed therewith and the mixture was moistened with a starch paste prepared from 5 kg of potato starch and distilled water, whereupon the mixture was granulated through a sieve. The granulate was dried and sieved, whereupon 2 kg of magnesium stearate was mixed into it. Finally the mixture was pressed into tablets each weighing 172 mg.

FORMULATION D. EFFERVESCING TABLETS 100 g of active substance, 140 g of finely divided citric acid, 100 g of finely divided sodium hydrogen carbonate, 3.5 g of magnesium stearate and flavouring agents (q.s) were mixed and the mixture was pressed into tablets each containing 100 mg of active substance.

FORMULATION E. SUSTAINED RELEASE TABLET 200 g of active substance were melted together with 50 g of stearic acid and 50 g of carnauba wax. The mixture thus obtained was cooled and ground to a particle size of at most 1 mm in diameter. The mixture thus obtained was mixed with 5 g of magnesium stearate and pressed into tablets each weighing 305 mg. Each tablet thus contains 200 mg of active substance.

FORMULATION F. INJECTION SOLUTION

| Active substance | 3.000 mg |
|---|---|
| Sodium pyrosulfite | 0.500 mg |
| Disodium edetate | 0.100 mg |
| Sodium chloride | 8.500 mg |
| Sterile water for inj. ad | 1.00 ml |

FORMULATION G. DEPOT PREPARATION

| Active substance (base/salt) | 200 mg |
|---|---|
| Ol. vegetabil. tenue (DAK 63) ad | 1 ml |

We claim:

1. A compound of the formula

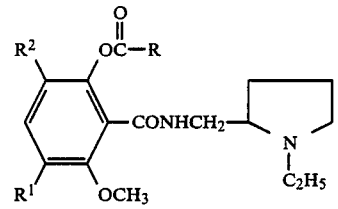

wherein R is a straight or branched alkyl group with 13–18 carbon atoms, $R^1$ is hydrogen, chlorine, bromine or an alkyl group with 1–3 carbon atoms and $R^2$ is chlorine, bromine or an alkyl group with 1–3 carbon atoms; or a physiologically acceptable salt or an optical isomer thereof.

2. A compound according to claim 1 in the form of an optical isomer thereof.

3. A compound according to any of claims 1 or 2 in the form of a physiologically acceptable salt thereof.

4. A pharmaceutical preparation comprising a carrier and as active ingredient a compound according to claim 1 or a physiologically acceptable salt or an optical isomer thereof in an amount of about 0.1 to 99% by weight of the preparation.

5. A pharmaceutical preparation according to claim 4 in dosage unit form.

6. A pharmaceutical preparation according to claims 4 or 5 comprising the active ingredient in association with a pharmaceutically acceptable carrier.

7. A pharmaceutical preparation according to claim 4 in the form of a depot preparation.

8. A pharmaceutical preparation according to claim 4 for subcutaneous or intramuscular administration.

9. A method for the treatment of emesis in man, characterized by the administration to a host in need of such treatment of an amount of a compound according to any one of claims 1 or 2 or a physiologically acceptable salt thereof effective to treat the symptoms of emesis.

10. A method for the treatment of psychosomatic diseases in man, characterized by the administration of a host in need of such treatment of an amount of a compound according to any of claims 1 or 2 or a physiologically acceptable salt thereof effective to treat the symptoms of psychosomatic diseases.

11. A method for the treatment of psychiatric disorders in man, characterized by the administration of a host in need of such treatment of an amount of a compound according to any of claims 1 or 2 or a physiologically acceptable salt thereof effective to treat the symptoms of psychiatric disorders.

* * * * *